United States Patent
Hosohata et al.

(10) Patent No.: US 12,128,016 B2
(45) Date of Patent: Oct. 29, 2024

(54) VANIN-1 INHIBITOR

(71) Applicant: EDUCATIONAL FOUNDATION OF OSAKA MEDICAL AND PHARMACEUTICAL UNIVERSITY, Takatsuki (JP)

(72) Inventors: Keiko Hosohata, Takatsuki (JP); Shinji Takai, Takatsuki (JP); Hiroki Yoneyama, Takatsuki (JP); Denan Jin, Takatsuki (JP); Yoshihide Usami, Takatsuki (JP)

(73) Assignee: EDUCATIONAL FOUNDATION OF OSAKA MEDICAL AND PHARMACEUTICAL UNIVERSITY, Takatsuki (JP)

( * ) Notice: Subject to any disclaimer, the term of this patent is extended or adjusted under 35 U.S.C. 154(b) by 0 days.

(21) Appl. No.: 18/696,857

(22) PCT Filed: Oct. 6, 2022

(86) PCT No.: PCT/JP2022/037384
§ 371 (c)(1),
(2) Date: Mar. 28, 2024

(87) PCT Pub. No.: WO2023/112440
PCT Pub. Date: Jun. 22, 2023

(65) Prior Publication Data
US 2024/0277639 A1    Aug. 22, 2024

(30) Foreign Application Priority Data
Dec. 17, 2021 (JP) ................... 2021-204876

(51) Int. Cl.
*A61K 31/165* (2006.01)

(52) U.S. Cl.
CPC .................. *A61K 31/165* (2013.01)

(58) Field of Classification Search
CPC .................................................. A61K 31/165
See application file for complete search history.

(56) References Cited

U.S. PATENT DOCUMENTS

2015/0250792 A1  9/2015  Muzerelle et al.
2018/0364233 A1  12/2018  Naquet et al.

FOREIGN PATENT DOCUMENTS

| JP | 2015-535832 A | 12/2015 |
| WO | WO 2011/152720 A1 | 12/2011 |
| WO | WO 2011/152721 A1 | 12/2011 |

OTHER PUBLICATIONS

International Search Report and Written Opinion dated Dec. 27, 2022 in International PCT Application No. PCT/JP2022/037384 in 10 pages.
Jansen et al., Discovery of small molecule vanin inhibitors: new tools to study metabolism and disease, ACS Chemical Biology, vol. 8, pp. 530-534, 2013.
Wedel et al., Pharmacological Inhibition of Vanin Activity Attenuates Transplant Vasculopathy in Rat Aortic Allografts, Transplantation, vol. 100, pp. 1656-1666, 2016.
Office Action dated Feb. 26, 2024 in Japanese Patent Application No. 2021-204876.

*Primary Examiner* — Umamaheswari Ramachandran
(74) *Attorney, Agent, or Firm* — Knobbe, Martens, Olson & Bear, LLP

(57) ABSTRACT

A Vanin-1 inhibitor includes as an active ingredient a pantotheine ketone derivative represented by the following Formula (I), wherein X, Y, Y', Z, and Z' are independently selected from a hydrogen atom, a fluorine group, and a substituent substituted with a fluorine group, and at least one of X, Y, Y', Z, or Z' is a fluorine group or a substituent substituted with a fluorine group.

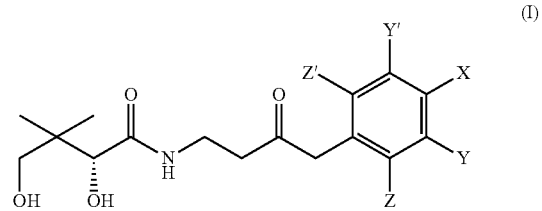

(I)

4 Claims, 5 Drawing Sheets

VANIN-1 INHIBITOR

CROSS REFERENCE TO RELATED APPLICATIONS

This application is the U.S. National Stage Application under 35 U.S.C. § 371 of International Application No. PCT/JP2022/037384, filed Oct. 6, 2022, which claims the benefit of Japanese Patent Application No. JP 2021-204876, filed Dec. 17, 2021. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present disclosure relates to a Vanin-1 inhibitor, particularly to a Vanin-1 inhibitor including a pantotheine ketone derivative as an active ingredient.

BACKGROUND ART

Vanin-1 is a GPI-anchored protein consisting of a base domain and a nitrilase domain and having 513 amino acids, and is an enzyme that catalyzes the hydrolysis reaction of pantetheine into pantothenic acid and cysteamine. Vanin-1 is primarily known to involve oxidative stress and regulation of inflammation.

For example, Non-patent literature 1 discloses RR6 as a Vanin-1 inhibitor. The structural formulae of pantetheine and RR6 are shown below.

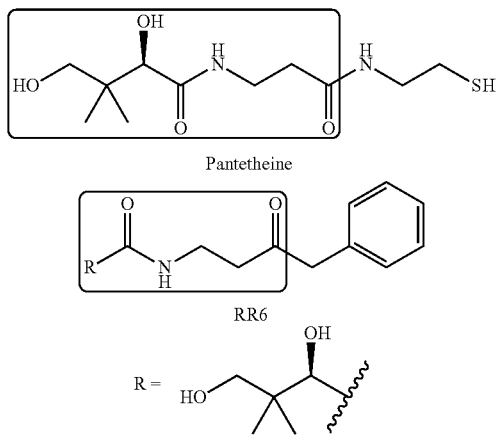

Pantetheine is a substrate for Vanin-1 that is an extracellular enzyme widely distributed in a living organism. As seen in the structural formulae shown above, RR6 has a structure in common with pantetheine.

Particularly, Non-patent literature 1 discloses that RR6 functions as a Vanin-1 inhibitor in an in vivo testing and that its inhibitory activity is expressed as $IC_{50}=0.78$ μM (see FIG. 3B in Non-patent literature 1).

Non-patent literature 2 discloses that therapies using Vanin-1 inhibitor RR6 exhibit a suppressive effect on vascular intimal thickening after aorta transplantation in a rat (see Abstract in Non-patent literature 2).

CITATION LIST

Non-Patent Literature

[Non-patent Literature 1] P. A. M. Jansen, J. A. Diepen, B. Ritzen, P. L. J. M. Zeeuwen, I. Cacciatore, C. Cornacchia, I. M. J. J. Vlijmen-Willems, E. Heuvel, P. N. M. Botman, R. H. Blaauw, P. H. H. Hermkens, F. P. J. T. Rutjes and J. Schalkwijk, Discovery of small molecule vanin inhibitors: new tools to study metabolism and disease, ACS Chem Biol. 8: 530-534, 2013.

[Non-patent Literature 2] Wedel J, Jansen P A, Botman P N, Rutjes F P, Schalkwijk J, Hillebrands J L., Pharmacological Inhibition of Vanin Activity Attenuates Transplant Vasculopathy in Rat Aortic Allografts, Transplantation, 100: 1656-1666, 2016.

SUMMARY OF INVENTION

Technical Problem

As described above, Non-patent literatures 1 and 2 disclose that RR6 functions as a Vanin-1 inhibitor and that therapies using RR6 exhibit a suppressive effect on vascular intimal thickening after aorta transplantation in a rat. In this respect, as described in Non-patent literature 2, RR6 requires to be administered as an active ingredient at a dose of 3 mg/mL in drinking water in order for RR6 to sufficiently function as a Vanin-1 inhibitor. Thus, the necessity to use high-dose RR6 was a problem. Therefore, there was a need for an inhibitor that has high Vanin-1 inhibitory activity and can sufficiently inhibit Vanin-1 at a low dose.

The present disclosure is made in view of the foregoing problem and an object of the present disclosure is to provide a Vanin-1 inhibitor that exceeds the Vanin-1 inhibitory activity of RR6 ($IC_{50}=0.78$ μM).

Solution to Problem

The inventors sought to develop a novel Vanin-1 inhibitor that exceeds the Vanin-1 inhibitory activity of RR6 ($IC_{50}=0.78$ μM) to achieve the object. Specifically, they used RR6 as a lead compound to synthesize compounds having different types and positions of various substituents and evaluate activity. As a result, they found that a Vanin-1 inhibitor exceeding the Vanin-1 inhibitory activity of RR6 was able to be provided by introducing at least one fluorine group or substituent substituted with a fluorine group onto the benzene ring of RR6, and reached the present disclosure.

Specifically, a Vanin-1 inhibitor according to the present disclosure includes as an active ingredient a pantotheine ketone derivative represented by the following Formula (I), wherein X, Y, Y', Z, and Z' are independently selected from a hydrogen atom, a fluorine group, and a substituent substituted with a fluorine group, and at least one of X, Y, Y', Z, or Z' is a fluorine group or a substituent substituted with a fluorine group.

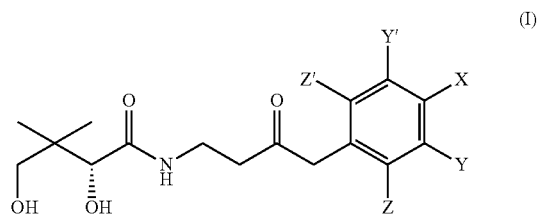

The Vanin-1 inhibitor according to the present disclosure can provide a Vanin-1 inhibitor that exhibits higher Vanin-1 inhibitory activity than the prior Vanin-1 inhibitor RR6. Thus, such Vanin-1 inhibitor can sufficiently inhibit Vanin-1 even when being at a low dose, and can be widely utilized as a Vanin-1 inhibitor having stronger inhibitory activity.

In the Vanin-1 inhibitor according to the present disclosure, the substituent substituted with a fluorine group in the pantotheine ketone derivative can be selected from the group consisting of an alkyl group having from 1 to 4 carbons and substituted with a fluorine group, an alkoxy group having from 1 to 4 carbons and substituted with a fluorine group, and an alkylthio group having from 1 to 4 carbons and substituted with a fluorine group.

In the Vanin-1 inhibitor according to the present disclosure, the substituent substituted with a fluorine group in the pantotheine ketone derivative can be selected from the group consisting of —$CF_3$, —$OCF_3$, and —$SCF_3$.

In the Vanin-1 inhibitor according to the present disclosure, only one of X, Y, Y', Z, or Z' in the pantotheine ketone derivative is a fluorine group or a substituent substituted with a fluorine group.

Advantageous Effects of Invention

The Vanin-1 inhibitor according to the present disclosure can provide a Vanin-1 inhibitor that exhibits higher Vanin-1 inhibitory activity than the prior Vanin-1 inhibitor RR6. Thus, such Vanin-1 inhibitor can sufficiently inhibit Vanin-1 even when being at a low dose, and can be widely utilized as a Vanin-1 inhibitor having stronger inhibitory activity.

DETAILED DESCRIPTION

Figure 1:
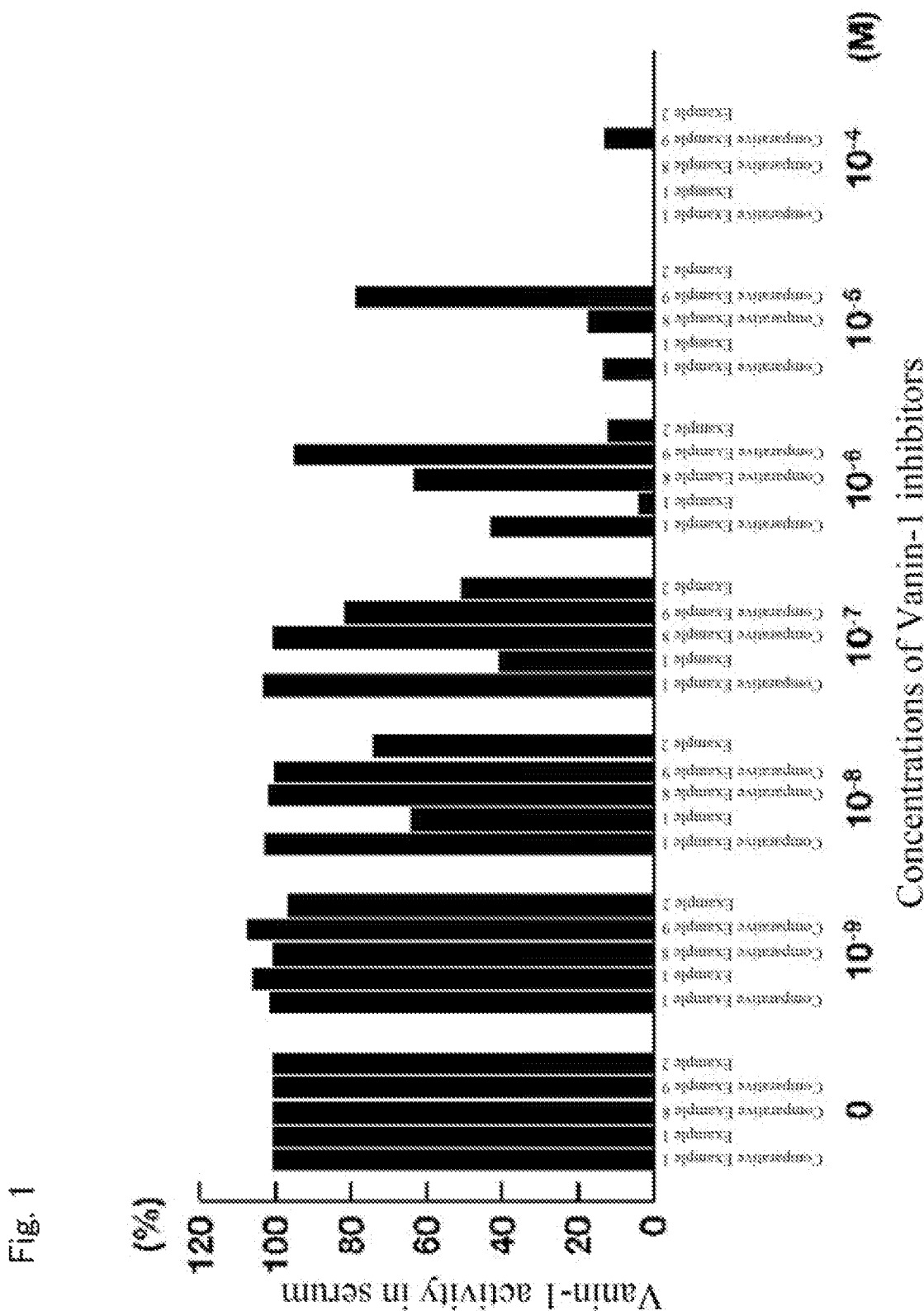
FIG. 1 is a graph showing results for in vitro Vanin-1 inhibitory activity of Vanin-1 inhibitors in Examples 1 to 2 and Comparative Examples 1, and 8 to 9.

Embodiments of the present disclosure are described below. The following description of preferred embodiments is merely an example in nature, and is not intended to limit the present disclosure, methods of applying the present disclosure, or use of the present disclosure.

A Vanin-1 inhibitor according to an embodiment will be described below.

As described above, Vanin-1 is an enzyme that catalyzes the hydrolysis reaction of pantetheine into pantothenic acid and cysteamine. As used herein, "Vanin-1 inhibition" refers to inhibition of enzyme activity of Vanin-1.

One embodiment of the present disclosure is directed to a Vanin-1 inhibitor including as an active ingredient a pantotheine ketone derivative represented by the following Formula (I).

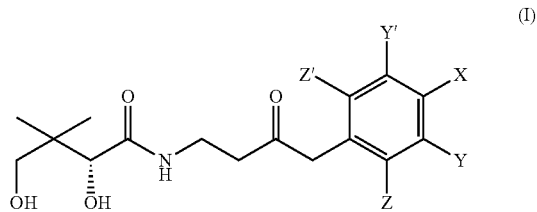

(I)

In Formula (I) as described above, X, Y, Y', Z, and Z' are independently selected from a hydrogen atom, a halogen group, an optionally substituted alkyl group having from 1 to 4 carbons, an optionally substituted alkoxy group having from 1 to 4 carbons, a nitro group, a cyano group, an optionally substituted alkylamino group having from 1 to 4 carbons, and a substituent substituted with a fluorine group, and at least one of X, Y, Y', Z, or Z' is a fluorine group or a substituent substituted with a fluorine group.

The halogen group of X, Y, Y', Z, and Z' includes a fluorine group, a chlorine group, a bromine group, an iodine group, and the like.

The optionally substituted alkyl group having from 1 to 4 carbons of X, Y, Y', Z, and Z' includes a methyl group, an ethyl group, an isopropyl group, a tert-butyl group, and the like.

The optionally substituted alkoxy group having from 1 to 4 carbons of X, Y, Y', Z, and Z' includes a methoxy group, an ethoxy group, a tert-butoxy group, and the like.

The optionally substituted alkylamino group having from 1 to 4 carbons of X, Y, Y', Z, and Z' includes a dimethylamino group, and the like.

The substituent substituted with a fluorine group of X, Y, Y', Z, and Z' includes an alkyl group having from 1 to 4 carbons and substituted with a fluorine group, an alkoxy group having from 1 to 4 carbons and substituted with a fluorine group, an alkylthio group having from 1 to 4 carbons and substituted with a fluorine group, and the like. It preferably includes a trifluoromethyl group (—$CF_3$), a trifluoromethoxy group (—$OCF_3$), and a trifluoromethylthio group (—$SCF_3$).

The at least one of X, Y, Y', Z, or Z' may require to be a fluorine group or a substituent substituted with a fluorine group, and the upper limit number of the substituents is not particularly limited. The remainder of the substituents can be independently selected appropriately from the groups of the substituents as described above. Also, only one of X, Y, Y', Z, or Z' may be a fluorine group or a substituent substituted with a fluorine group. In this case, the remainder of the substituents can also be independently selected appropriately from the groups of the substituents as described above.

[Specific Examples of Pantotheine Ketone Derivatives Represented by Formula (I)]

Specific examples of pantotheine ketone derivatives represented by Formula (I) include, for example, the following compounds.

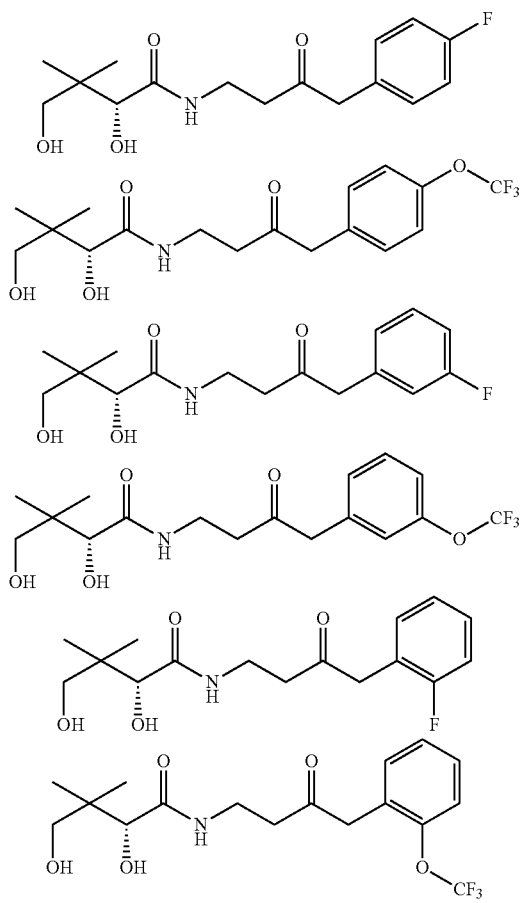

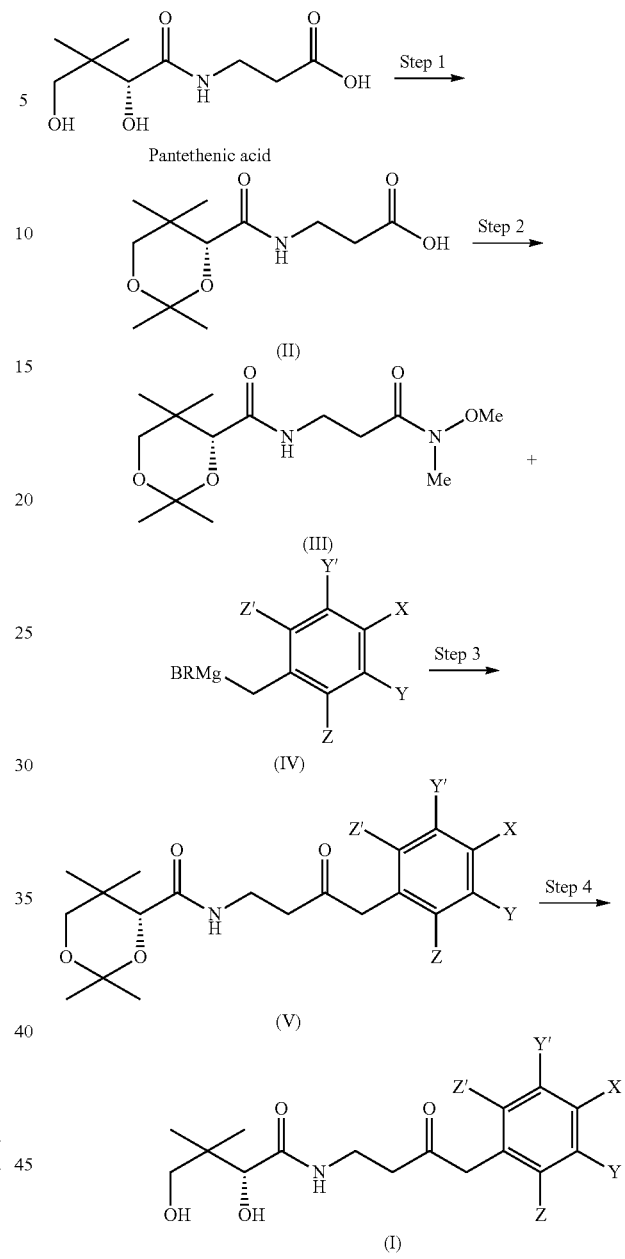

In the embodiment, the Vanin-1 inhibitor may be one that includes as an active ingredient a pantotheine ketone derivative represented by Formula (I), and the amount of the pantotheine ketone derivative contained is not particularly limited.

In the embodiment, the Vanin-1 inhibitor has a dosage form that is not particularly limited and includes, for example, tablets, capsules, powders, granules, liquids, or oral preparations such as sublingual preparations, injectables, ointments, patches, suppositories, aerosols, or the like.

In the embodiment, formulation can be carried out by using well-known formulation techniques, and the Vanin-1 inhibitor can include suitable formulation additives. The formulation additive includes, but is not limited to, excipients, suspending agents, emulsifying agents, preservatives, pH adjusting agents, flavoring agents, and the like, and those used in the art can be appropriately utilized.

[Method for Producing Pantotheine Ketone Derivatives Represented by Formula (I)]

Methods for producing a pantotheine ketone derivative that is an active ingredient of the Vanin-1 inhibitor according to the embodiment are not particularly limited and conventionally well-known methods can be appropriately used. One embodiment of a method for producing a pantotheine ketone derivative is described below.

In the embodiment, a pantotheine ketone derivative represented by Formula (I) can be produced by, for example, steps 1 to 4 as follows.

(Step 1)
Pantethenic acid is reacted with an acid catalyst, such as concentrated sulfuric acid, in an acetone solvent at room temperature to produce a compound (II).

(Step 2)
The compound (II) is reacted with N,O-dimethylhydroxylamine and hydrochloride thereof in the presence of a base, such as triethylamine, ethyldiisopropylamine, DBU (diazabicycloundecene), in a solvent, such as dichloromethane, dimethylformamide, tetrahydrofuran, toluene, dioxane, or a mixture thereof, at a temperature ranging from 0° C. to 250° C., by using a dehydrating and condensing agent, such as N,N'-dicyclohexylcarbodiimide, 1-ethyl-3-(3-dimethylaminopropyl)carbodiimide hydrochloride, according to a method described in the literature (Schalkwijk, J. et al., ACS Chem. Biol., 2013, 8, 530-534), to produce a compound (III).

(Step 3)

The compound (III) is reacted with a compound (IV) (wherein X, Y, Y', Z, and Z' are independently selected from a hydrogen atom, a halogen group, an optionally substituted alkyl group having from 1 to 4 carbons, an optionally substituted alkoxy group having from 1 to 4 carbons, a nitro group, a cyano group, an optionally substituted alkylamino group having from 1 to 4 carbons, and a substituent substituted with a fluorine group, and at least one of X, Y, Y', Z, or Z' is a fluorine group or a substituent substituted with a fluorine group) in a solvent, such as diethylether, tetrahydrofuran, toluene, dioxane, or a mixture thereof, at a temperature ranging from −78° C. to 200° C., to produce a compound (V).

(Step 4)

Deprotection of an acetal group in the compound (V) is performed to produce a pantotheine ketone derivative represented by Formula (I).

The pantotheine ketone derivative represented by Formula (I) is produced by such steps and can be isolated and purified through a purification means, such as column chromatography, to utilize it. In this regard, the purification means for the pantotheine ketone derivative are not particularly limited and purification means known in the art can be appropriately used.

EXAMPLES

Examples for explaining in detail a Vanin-1 inhibitor according to the present disclosure are presented below.

Example 1

A pantotheine ketone derivative (OMP-7) represented by Formula (I), wherein X was —OCF$_3$ and Y, Y', Z, and Z' were a hydrogen atom, was produced as follows.

Production of (R)-3-(2,2,5,5-tetramethyl-1,3-dioxane-4-carboxamide)propanoic acid According to a method described in the literature (Schalkwijk, J. et al., ACS Chem. Biol., 2013, 8, 530-534), 25 g of (R)-calcium pantethenate was dissolved in 120 mL of 1N hydrochloric acid solution, salt was added to the solution until saturation, extraction with ethyl acetate was performed, and the organic layer was dried over anhydrous sodium sulfate. After distillation of the solvent, the resulting pantethenic acid was dissolved in 500 mL of acetone, and 0.5 mL of concentrated sulfuric acid was added to stir at room temperature for 15 hours. After adding sodium bicarbonate to stop the reaction, filtration was performed, and the solvent was distilled from the filtrate to obtain a compound of interest.

Spectral data: 1H-NMR (CDCl3): δ0.99 (S, 3H), 1.05 (S, 3H), 1.45 (s, 3H), 1.48 (s, 3H), 2.63 (t, 2H, J=6.2 Hz), 3.30 (d, 1H, J=11.7 Hz), 3.56 (m, 2H), 3.71 (d, 1H, J=11.7 Hz), 4.13 (s, 1H), 7.07 (t, 1H, J=6.0 Hz); 13C-NMR (CDCl3): δ 18.7, 18.8, 22.0, 29.4, 32.9, 33.9, 34.1, 71.4, 77.1, 99.1, 170.2, 176.7.

Production of (R)—N-{3-[methoxy(methyl)amino]-3-oxopropyl}-2,2,5,5-tetramethyl-1,3-dioxane-4-carboxamide Dissolution of 4.1 g of the compound obtained was performed in 50 mL of dichloromethane, and 4.5 g of 1-ethyl-3-(3-dimethylaminopropyl)carbodiimide hydrochloride, 2.3 g of N,O-dimethylhydroxylamine hydrochloride, 1.0 g of dimethylaminopyridine, and 8 mL of N,N-diisopropylethylamine were added to stir at room temperature for 20 hours. After adding a saturated ammonium chloride solution to stop the reaction, extraction with ethyl acetate was performed and the organic layer was dried over anhydrous sodium sulfate. After distillation of the solvent, silica gel column chromatography (ethyl acetate) was used for purification and 4.4 g of compound of interest was obtained as a compound in the form of pale yellow oil.

1H-NMR (CDCl3): δ0.96 (s, 3H), 1.03 (s, 3H), 1.42 (s, 3H), 1.46 (s, 3H), 2.76-2.59 (m, 2H), 3.18 (s, 3H), 3.27 (d, 1H, J=11.7 Hz), 3.64-3.48 (m, 2H), 3.67 (s, 3H), 3.68 (d, 1H, J=11.7 Hz), 4.07 (s, 1H), 7.13 (t, 1H, J=5.7 Hz); 13C-NMR (CDCl3): δ18.7, 18.8, 22.1, 29.4, 31.8, 32.1, 33.0, 34.0, 61.2, 71.5, 77.1, 99.0, 169.9, 172.9.

Production of (R)-2,2,5,5-tetramethyl-N-[3-oxo-4-(4-trifluoromethoxyphenyl)butyl]-1,3-dioxane-4-carboxamide Dissolution of 0.9 g of the compound obtained was performed in 30 mL of THF, and 2.5 g of 4-(trifluoromethoxy)benzyl bromide and 0.3 g of magnesium turnings were added to stir at room temperature for 2 hours. After adding a saturated ammonium chloride solution to stop the reaction, extraction with ethyl acetate was performed and the organic layer was dried over anhydrous sodium sulfate. After distillation of the solvent, silica gel column chromatography (ethyl acetate:hexane=1:1) was used for purification and 1.0 g of compound of interest was obtained as a compound in the form of pale yellow oil. 1H-NMR (CDCl3): δ0.87 (s, 3H), 1.01 (s, 3H), 1.41 (s, 3H), 1.45 (s, 3H), 2.68-2.83 (m, 2H), 3.26 (d, 1H, J=11.6 Hz), 3.39-3.59 (m, 2H), 3.67 (d, 1H, J=11.6 Hz), 3.71 (s, 2H), 4.04 (s, 1H), 6.90 (br, 1H), 7.18 (d, 2H, J=8.8 Hz), 7.22 (d, 2H, J=8.8 Hz); 13C-NMR (CDCl3): δ18.6, 18.7, 22.0, 29.4, 32.9, 33.2, 41.6, 49.1, 71.4, 99.0, 120.4 (quartet, J=257 Hz), 121.3, 130.7, 132.3, 148.3, 169.8, 206.6.

Production of (R)-2,4-dihydroxy-3,3-dimethyl-N-[3-oxo-4-(4-trifluoromethoxyphenyl)butyl]butanamide (OMP-7)

Dissolution of 1.0 g of the compound obtained was performed in 20 mL of acetonitrile, and 0.1 g of bismuth chloride (III) and 1 mL of water were added to stir at room temperature for 14 hours. The reaction mixture was absorbed into diatomaceous earth and excessive solvent was concentrated under reduced pressure before purification by silica gel column chromatography (ethyl acetate), and 0.7 g of compound of interest (OMP-7) was obtained as a compound in the form of pale yellow oil. 1H-NMR (CDCl3): δ0.83 (s, 3H), 0.93 (s, 3H), 2.76 (t, 2H, J=5.6 Hz), 3.42-3.58 (m, 4H), 3.72 (s, 2H), 3.95 (d, 1H, J=4.8 Hz), 4.02 (d, 1H, J=4.8 Hz), 7.18 (d, 2H, J=9.2 Hz), 7.21 (d, 2H, J=9.2 Hz); 13C-NMR (CDCl3): δ20.1, 21.0, 21.1, 33.6, 39.2, 41.6, 49.0, 71.1, 120.4 (quartet, J=257 Hz), 121.2, 130.8, 132.1, 148.3, 173.2, 206.9.

Example 2

A pantotheine ketone derivative (OMP-10) represented by Formula (I), wherein X was a fluorine group and Y, Y', Z, and Z' were a hydrogen atom, was obtained in a manner similar to that described in Example 1, except for the addition of 4-fluorobenzyl bromide instead of 4-(trifluoromethoxy)benzyl bromide.

Example 3

A pantotheine ketone derivative (OMP-11) represented by Formula (I), wherein X was a hydrogen atom, Y was —OCF$_3$, and Y', Z, and Z' were a hydrogen atom, was obtained in a manner similar to that described in Example 1 except for the addition of 3-(trifluoromethoxy)benzyl bromide instead of 4-(trifluoromethoxy)benzyl bromide.

Example 4

A pantotheine ketone derivative (OMP-13) represented by Formula (I), wherein X was a hydrogen atom, Y was a fluorine group, and Y', Z, and Z' were a hydrogen atom, was obtained in a manner similar to that described in Example 1, except for the addition of 3-fluorobenzyl bromide instead of 4-(trifluoromethoxy)benzyl bromide.

Example 5

A pantotheine ketone derivative (OMP-14) represented by Formula (I), wherein X, Y, and Y' were a hydrogen atom, Z was a fluorine group, and Z' was a hydrogen atom, was obtained in a manner similar to that described in Example 1, except for the addition of 2-fluorobenzyl bromide instead of 4-(trifluoromethoxy)benzyl bromide.

Comparative Example 1

A pantotheine ketone derivative (RR6) was obtained in a manner similar to that described in Example 1, except for the addition of benzyl bromide instead of 4-(trifluoromethoxy)benzyl bromide.

Comparative Example 2

A pantotheine ketone derivative (OMP-1) was obtained in a manner similar to that described in Example 1, except for the addition of 4-chlorobenzyl bromide instead of 4-(trifluoromethoxy)benzyl bromide.

Comparative Example 3

A pantotheine ketone derivative (OMP-2) was obtained in a manner similar to that described in Example 1, except for the addition of 4-methoxybenzyl bromide instead of 4-(trifluoromethoxy)benzyl bromide.

Comparative Example 4

A pantotheine ketone derivative (OMP-3) was obtained in a manner similar to that described in Example 1, except for the addition of 4-methylbenzyl bromide instead of 4-(trifluoromethoxy)benzyl bromide.

Comparative Example 5

A pantotheine ketone derivative (OMP-4) was obtained in a manner similar to that described in Example 1, except for the addition of 3,4-dichlorobenzyl bromide instead of 4-(trifluoromethoxy)benzyl bromide.

Comparative Example 6

A pantotheine ketone derivative (OMP-5) was obtained in a manner similar to that described in Example 1, except for the addition of 2-(bromomethyl)naphthalen instead of 4-(trifluoromethoxy)benzyl bromide.

Comparative Example 7

A pantotheine ketone derivative (OMP-6) was obtained in a manner similar to that described in Example 1, except for the addition of 1-(bromomethyl)naphthalen instead of 4-(trifluoromethoxy)benzyl bromide.

Comparative Example 8

A pantotheine ketone derivative (OMP-8) was obtained as a byproduct of OMP-9 in a manner similar to that described in Example 1, except for the addition of (3-bromo-1-propynyl)trimethylsilane instead of 4-(trifluoromethoxy)benzyl bromide.

Comparative Example 9

A pantotheine ketone derivative (OMP-9) was obtained together with OMP-8 in a manner similar to that described in Example 1, except for the addition of (3-bromo-1-propynyl)trimethylsilane instead of 4-(trifluoromethoxy)benzyl bromide.

The pantotheine ketone derivatives obtained in Examples 1 to 5 and Comparative Examples 1 to 9 are listed in Table 1.

TABLE 1

| Example/Comparative Example | Sample Name | Structural Formula |
|---|---|---|
| Example 1 | OMP-7 | 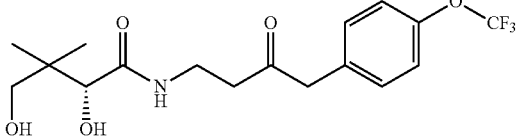 |
| Example 2 | OMP-10 | 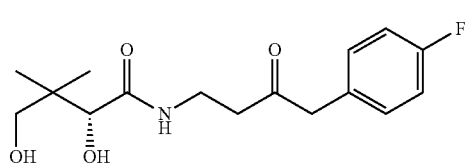 [SMILES: CC(C)(CO)[C@@H](O)C(=O)NCCC(=O)Cc1ccc(F)cc1] |

TABLE 1-continued

| Example/Comparative Example | Sample Name | Structural Formula |
|---|---|---|
| Example 3 | OMP-11 | 3-(trifluoromethoxy)phenyl derivative of (2S)-2,4-dihydroxy-3,3-dimethyl-N-[3-oxo-4-aryl-butyl]butanamide |
| Example 4 | OMP-13 | 3-fluorophenyl derivative |
| Example 5 | OMP-14 | 2-fluorophenyl derivative |
| Comparative Example 1 | RR6 | phenyl derivative |
| Comparative Example 2 | OMP-1 | 4-chlorophenyl derivative |
| Comparative Example 3 | OMP-2 | 4-methoxyphenyl derivative |
| Comparative Example 4 | OMP-3 | 4-methylphenyl derivative |
| Comparative Example 5 | OMP-4 | 3,4-dichlorophenyl derivative |
| Comparative Example 6 | OMP-5 | 2-naphthyl derivative |

TABLE 1-continued

| Example/Comparative Example | Sample Name | Structural Formula |
|---|---|---|
| Comparative Example 7 | OMP-6 | (structure: pantoyl amide linked to propyl ketone bearing CH$_2$-naphthyl group) |
| Comparative Example 8 | OMP-8 | (structure: pantoyl amide linked to chain terminating in enol –C(OH)=CH–CH$_3$) |
| Comparative Example 9 | OMP-9 | (structure: pantoyl amide linked to chain terminating in vinyl ketone CH=CH$_2$) |

[In Vitro Measurement of Vanin-1 Inhibitory Activity]

The pantotheine ketone derivatives obtained in Examples 1 to 5 and Comparative Examples 1 to 9 were used as a Vanin-1 inhibitor to measure Vanin-1 inhibitory activity in vitro as follows.

(Material)

A 9 g/package phosphate buffer powder (1/15 molL$^{-1}$=66 mM, Wako Pure Chemical) was dissolved in 1 L of distilled water to produce an assay buffer. Pantothenate-AMC serving as a substrate was synthesized according to protocols as described in Analytical Biochemistry 2010; 399: 284-292. For use as human serum, "normal human serum" was purchased from KOHJIN BIO (product number: 12181211).

(Screening Using Human Serum)

Vanin-1 inhibitory activity was measured in accordance with the following steps 1 to 8 of:
1. introducing 79 µL of assay buffer in a 96-well black plate,
2. adding 10 µL of human serum to the wells containing the assay buffer,
3. adding 1 µL of each Vanin-1 inhibitor (10$^{-7}$ M to 10$^{-2}$ M in DMSO) or 1 µL of DMSO to the wells from the step [2.],
4. adding 10 µL of 1 mM Pantothenate-AMC to the wells from the step [3.],
5. measuring at Ex=390 nm and Ex=465 nm before incubation,
6. incubating at 37° C. for 30 minutes,
7. measuring at Ex=390 nm and Ex=465 nm,
8. subtracting fluorescence after 0 minute incubation, from fluorescence after 30 minutes incubation, to express Vanin-1 inhibitory activity of each inhibitor in percent with respect to that of DMSO being 100%.

(Results)

FIGS. 1 to 4 shows results for Vanin-1 inhibitory activity measured by using the steps described above. FIG. 1 shows Vanin-1 inhibitory activity of Examples 1 to 2 and Comparative Examples 1, and 8 to 9. As shown in FIG. 1, the pantotheine ketone derivatives of Examples 1 and 2 inhibited Vanin-1 activity lower than the pantotheine ketone derivative of Comparative Example 1, and were found to have very high Vanin-1 inhibitory activity. Specifically, it was found that the Vanin-1 inhibitory activity of Example 1 was IC$_{50}$=0.035 µM, the Vanin-1 inhibitory activity of Example 2 was IC$_{50}$=0.12 µM, and the Vanin-1 inhibitory activity of Comparative Example 1 was IC$_{50}$=0.78 µM. Therefore, it was identified that the Vanin-1 inhibitory activity of the pantothein ketone derivative of Example 1 was about 20 times that of Comparative Example 1, and the Vanin-1 inhibitory activity of the pantothein ketone derivative of Example 2 was about 6 times that of Comparative Example 1. It was thus found that the introduction of a fluorine group or a trifluoromethoxy group onto the benzene ring of RR6, a prior Vanin-1 inhibitor, significantly improved Vanin-1 inhibitory activity. In contrast, the Vanin-1 inhibitory activity of Comparative Examples 8 and 9 was found to be lower than that of Comparative Example 1. Therefore, it was shown that the presence of the benzene ring in pantotheine ketone derivatives was necessary for good Vanin-1 inhibitory activity.

Figure 2:
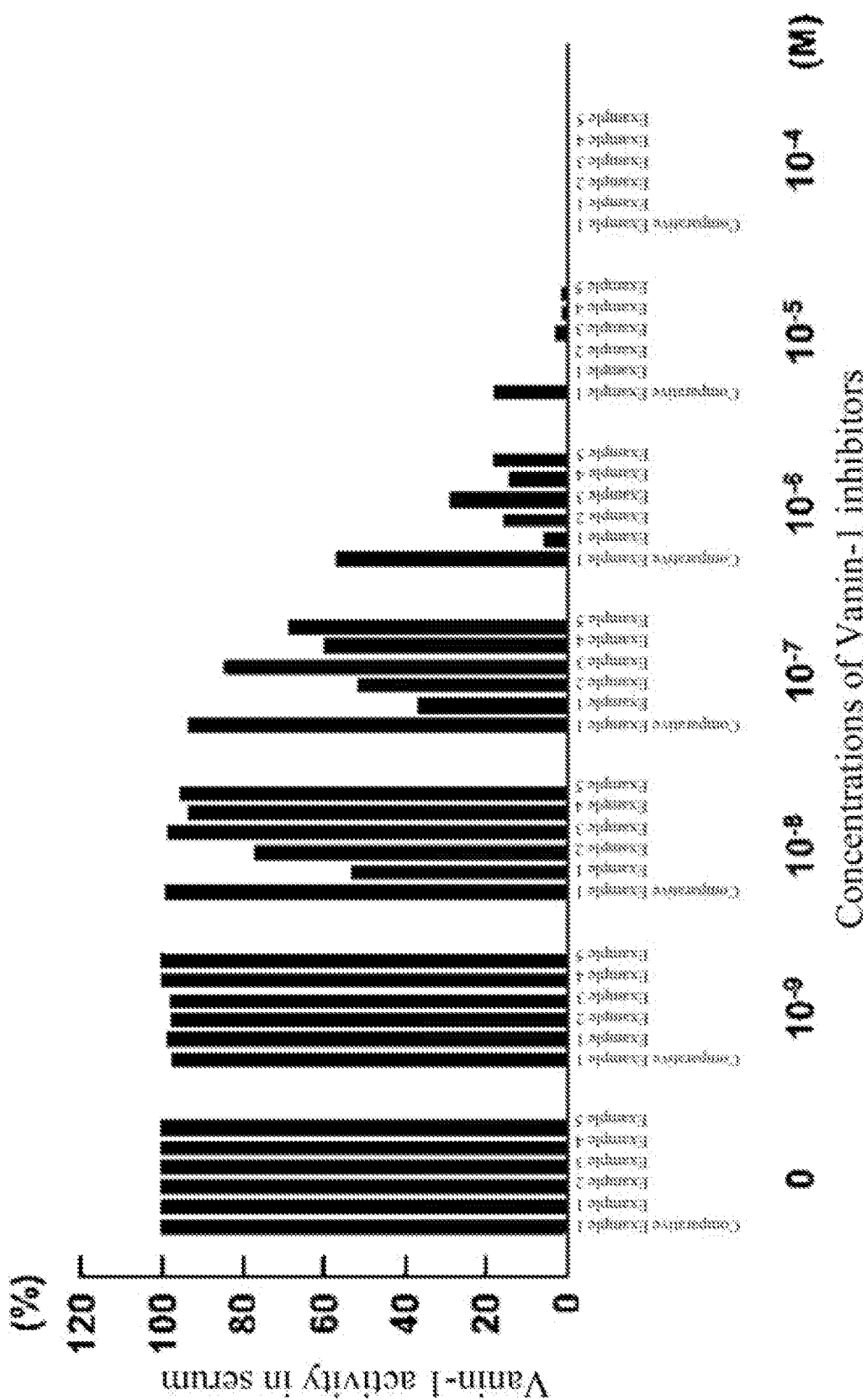
FIG. 2 is a graph showing results for in vitro Vanin-1 inhibitory activity of Vanin-1 inhibitors in Examples 1 to 5 and Comparative Example 1.

FIG. 2 shows Vanin-1 inhibitory activity of Examples 1 to 5 and Comparative Example 1. As shown in FIG. 2, it was found that the Vanin-1 inhibitors of Examples 1 to 5 all had higher Vanin-1 inhibitory activity than that of Comparative Example 1. Therefore, it was found that the position of the trifluoromethoxy group or fluorine group on the benzene ring in the pantotheine ketone derivatives according to the present examples was not restricted to the para position and in the cases of the ortho position and the meta position, good Vanin-1 inhibitory activity was shown.

Figure 3:
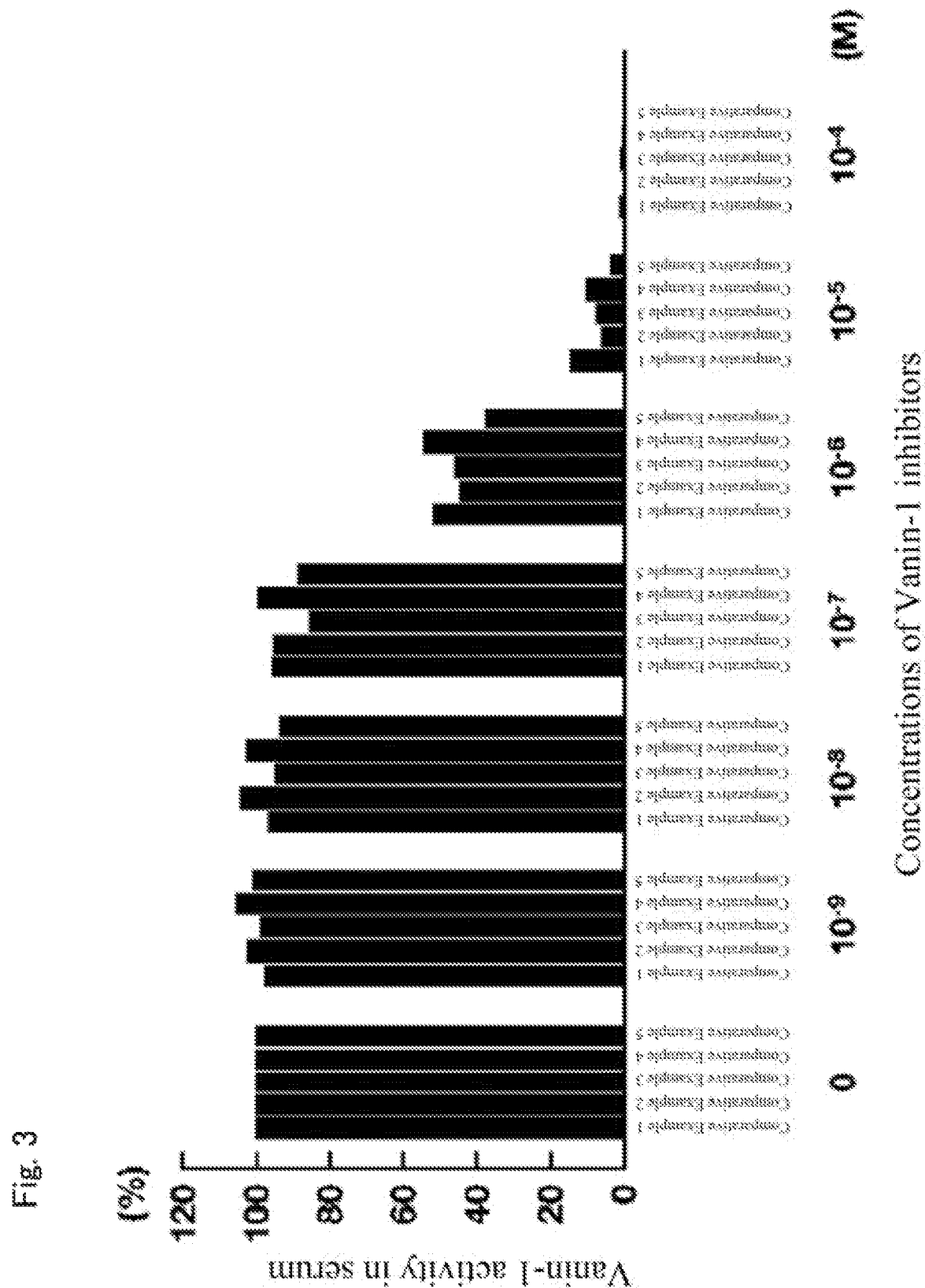
FIG. 3 is a graph showing results for in vitro Vanin-1 inhibitory activity of Vanin-1 inhibitors in Comparative Examples 1 to 5.

FIG. 3 shows Vanin-1 inhibitory activity of Comparative Examples 1 to 5. As shown in FIG. 3, it was found that no significant differences were observed in the Vanin-1 inhibitory activity of Comparative Examples 1 to 5. Therefore, it was identified that the presence of at least one fluorine group or substituent substituted with a fluorine group on the benzene ring of the pantotheine ketone derivative was necessary for good Vanin-1 inhibitory activity.

Figure 4:
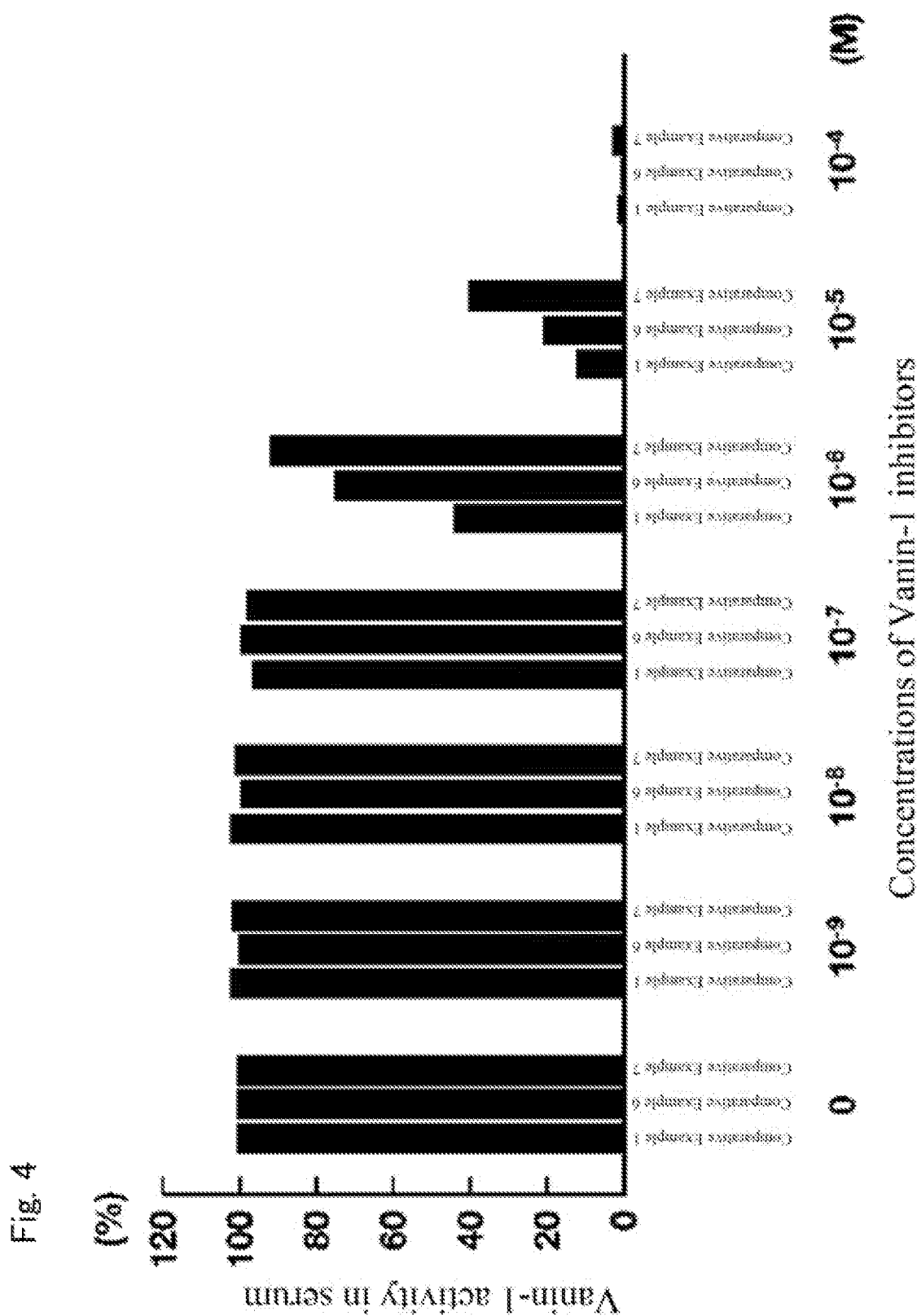
FIG. 4 is a graph showing results for in vitro Vanin-1 inhibitory activity of Vanin-1 inhibitors in Comparative Examples 1, and 6 to 7.

FIG. 4 shows Vanin-1 inhibitory activity of Comparative Examples 1, and 6 to 7. As shown in FIG. 4, the Vanin-1 inhibitory activity of Comparative Examples 6 and 7 was found to be lower than that of Comparative Example 1. It was thus identified that the aromatic ring moiety of the pantotheine ketone derivative was preferably a benzene ring.

From the results described above, it was shown that the pantotheine ketone derivatives of Examples 1 to 5 were Vanin-1 inhibitors that had stronger inhibitory activity in vitro than the pantotheine ketone derivatives of Comparative Examples 1 to 9.

[In Vivo Measurement of Vanin-1 Inhibitory Activity]

The pantotheine ketone derivatives obtained in Example 1 and Comparative Example 1 were used as a Vanin-1 inhibitor to measure Vanin-1 inhibitory activity in vivo as follows.

(Material)

An assay buffer and substrate were the same as those used in the in vitro measurement of activity described above. Hamsters used were 6-week-old male Syrian hamsters purchased from Japan SLC.

(Measurement of Inhibitory Activity in Sera and Kidney Tissues Using Hamsters)

The pantotheine ketone derivatives of Example 1 and Comparative Example 1 at a dose of 10 mg/kg were each administered by subcutaneous injection in the backs of different hamsters, and 1 hour and 4 hours after the administration, blood collection and kidney removal were performed under anesthesia. The blood and kidney of the normal hamsters were indicated as Normal. The blood was refrigerated overnight at 4° C. and then centrifuged at 3000 rpm for 20 minutes at 4° C., and the supernatant was used as serum. The kidney was homogenized in an assay buffer in an amount 10 times the tissue weight, and centrifuged at 8000 rpm for 30 minutes at 4° C., and the supernatant was used as a kidney tissue extract. Proteins in the kidney tissue were quantified by using a BCA protein assay (Thermo Fishers Scientific).

Vanin-1 inhibitory activity was measured in accordance with the following steps 1 to 7 of:
1. introducing 80 µL of assay buffer in a 96-well black plate,
2. adding 10 µL of serum or kidney tissue extract to the wells containing the assay buffer,
3. adding 10 µL of 1 mM Pantothenate-AMC to the wells from the step [2.],
4. measuring at Ex=390 nm and Ex=465 nm before incubation,
5. incubating at 37° C. for 30 minutes,
6. measuring at Ex=390 nm and Ex=465 nm,
7. subtracting fluorescence after 0 minute incubation, from fluorescence value after 30 minutes incubation, and calculating enzyme unit (U) using as an index the amount of AMC produced per minute with respect to the fluorescence value of 40 µM AMC as a reference. The Vanin-1 activity in the kidney tissue extracts was further calculated to normalize by the protein concentration.

(Results)

Figure 5:
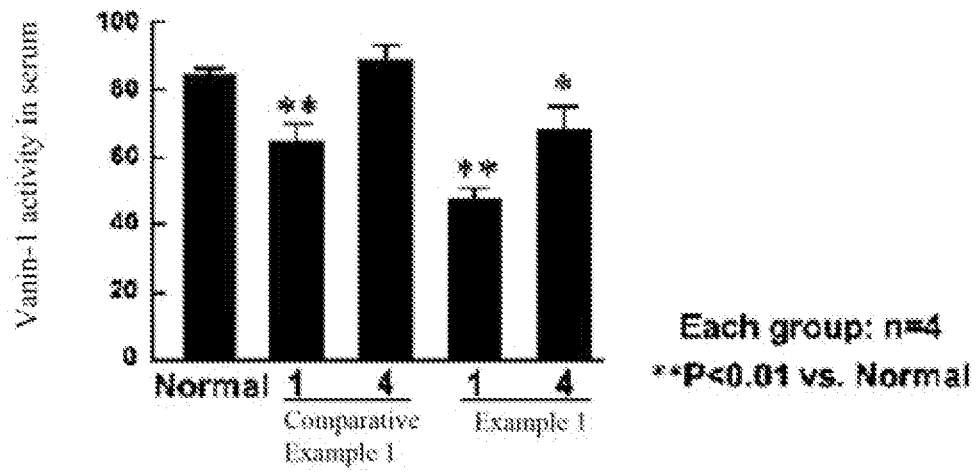
FIG. 5 shows results for in vivo Vanin-1 inhibitory activity of Vanin-1 inhibitors in Example 1 and Comparative Example 1, and demonstrates Vanin-1 inhibitory activity in sera in graph (a) and Vanin-1 inhibitory activity in extracts from kidney tissues in graph (b).
Figure 5:
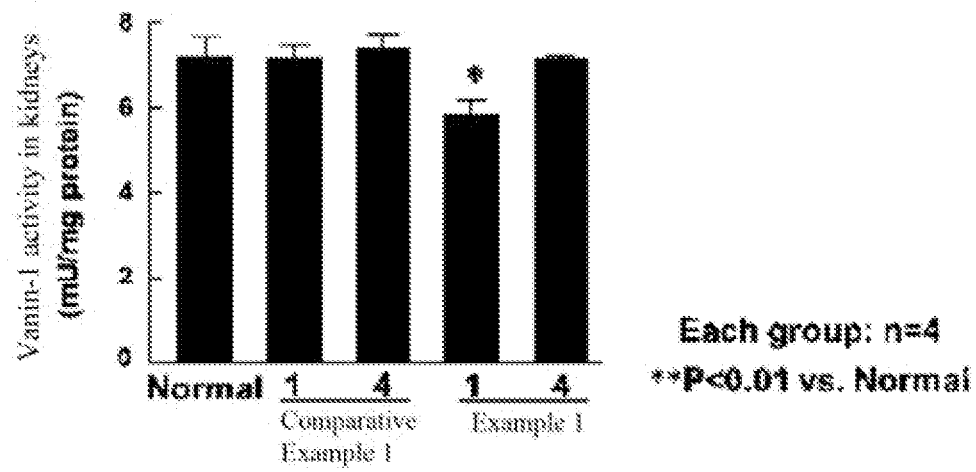

FIG. 5 shows results for Vanin-1 inhibitory activity of the pantotheine ketone derivatives from Example 1 and Comparative Example 1 as measured by using the steps described above, and FIG. 5a presents Vanin-1 inhibitory activity in sera. As shown in FIG. 5a, it was found that the Vanin-1 activity was suppressed in the sera 1 hour after administrating each of the Vanin-1 inhibitors of Example 1 and Comparative Example 1. Particularly, it was shown that the Vanin-1 inhibitor of Example 1 suppressed Vanin-1 activity lower than that of Comparative Example 1. It was also shown that in the case of the sera 4 hours after administrating the Vanin-1 inhibitors, the activity value returned to normal value regarding Comparative Example 1; however, the Vanin-1 activity was suppressed below the normal value regarding Example 1. It was thus found that the Vanin-1 inhibitor of Example 1 maintained Vanin-1 inhibitory activity in sera even 4 hours after administrating to the hamsters.

FIG. 5b presents Vanin-1 inhibitory activity in kidney tissue extracts. As shown in FIG. 5b, it was found that the Vanin-1 activity was same as the normal value and Vanin-1 was not able to be inhibited in the kidney tissues 1 hour and 4 hours after administrating the Vanin-1 inhibitor of Comparative Example 1. In contrast, it was found that the Vanin-1 inhibitor of Example 1 was able to inhibit Vanin-1 in the kidney tissues 1 hour after administrating the Vanin-1 inhibitor. It was identified that whereas the Vanin-1 activity returned to the normal value in the kidney tissues 4 hours after administrating the Vanin-1 inhibitor of Example 1, the Vanin-1 inhibitory activity of the Vanin-1 inhibitor of Example 1 was much higher than that of Comparative Example 1.

From the results as described above, it was shown that the pantotheine ketone derivative of Example 1 was a Vanin-1 inhibitor that had stronger inhibitory activity in vivo than the pantotheine ketone derivative of Comparative Example 1.

What is claimed is:

1. A Vanin-1 inhibitor is a pantotheine ketone derivative represented by Formula (I), wherein X, Y, Y', Z, and Z' are independently selected from a hydrogen atom, a fluorine group and at least one of X, Y, Y', Z, or Z' is a fluorine group or a substituent substituted with a fluorine group selected from the group consisting of an alkyl group having from 1 to 4 carbons and substituted with a fluorine group, an alkoxy group having from 1 to 4 carbons and substituted with a fluorine group, and an alkylthio group having from 1 to 4 carbons and substituted with a fluorine group,

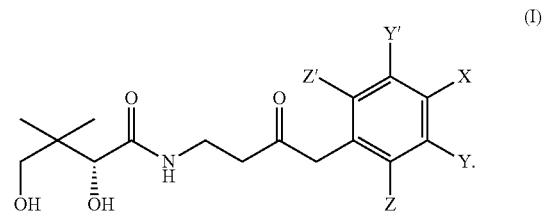

2. The Vanin-1 inhibitor according to claim 1, wherein the substituent substituted with a fluorine group is selected from the group consisting of —CF$_3$, —OCF$_3$, and —SCF$_3$.

3. The Vanin-1 inhibitor according to claim 1, wherein at least one of X, Y, Y', Z, or Z' is a fluorine group.

4. The Vanin-1 inhibitor according to claim 1, wherein at least one of X, Y, Y', Z, or Z' is a substituent substituted with a fluorine group selected from the group consisting of an alkyl group having from 1 to 4 carbons and substituted with a fluorine group, an alkoxy group having from 1 to 4 carbons and substituted with a fluorine group, and an alkylthio group having from 1 to 4 carbons and substituted with a fluorine group.

* * * * *